United States Patent
Nair et al.

(10) Patent No.: US 7,772,195 B2
(45) Date of Patent: *Aug. 10, 2010

(54) METHODS AND COMPOSITIONS FOR THE TREATMENT OF OBESITY, INSULIN RELATED DISEASES AND HYPERCHOLESTEROLEMIA

(75) Inventors: Muraleedharan G. Nair, Okemos, MI (US); Bolleddula Jayaprakasam, East Lansing, MI (US); Lawrence K. Olson, East Lansing, MI (US); Robert E. Schutzki, Eaton Rapids, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 384 days.

This patent is subject to a terminal disclaimer.

(21) Appl. No.: 11/072,151

(22) Filed: Mar. 4, 2005

(65) Prior Publication Data

US 2006/0025354 A1    Feb. 2, 2006

Related U.S. Application Data

(60) Provisional application No. 60/591,806, filed on Jul. 29, 2004.

(51) Int. Cl.
*A61K 31/7048* (2006.01)
*A61K 31/57* (2006.01)
*A61K 31/353* (2006.01)

(52) U.S. Cl. .................. 514/27; 514/171; 514/456; 514/559

(58) Field of Classification Search ............. 514/27, 514/171, 456, 559
See application file for complete search history.

(56) References Cited

U.S. PATENT DOCUMENTS 4,229,439 A * 10/1980 Majoie .................. 514/27
2004/0131749 A1 * 7/2004 Grabiel et al. ........... 426/629

FOREIGN PATENT DOCUMENTS

| WO | WO 02/24212 | * | 3/2002 |
| WO | WO 03/039270 | * | 5/2003 |
| WO | WO 03039270 | * | 5/2003 |

OTHER PUBLICATIONS

Tsuda et al et al J. Nutrition, 2003, 133, 2125-2130.*
Nair et al, Agricultural and Food Chemistry, 2002, 50, 2519-2523.*
A. Vanella et al, Cell Biology and Toxicology, 2003, 19, 243-252.*
Jayaprakasam, B. et al., J. Agric. Food Chem. 53, pp. 28-31 (2005).
Jayaprakasam, B. et al., J. Agric. Food Chem. 54, pp. 243-248 (2006).

* cited by examiner

*Primary Examiner*—Shaojia Anna Jiang
*Assistant Examiner*—Ganapathy Krishnan
(74) *Attorney, Agent, or Firm*—Avery N. Goldstein

(57) ABSTRACT

A method for the treatment of obesity, diabetes, high cholesterol and related diseases including hyperglycemia, lipid disorders, hyperglyceridemia, dyslipidemia and atherosclerosis in mammals using anthocyanins, anthocyanidins, ursolic acid and/or betulinic acid is described. Compositions adapted for these treatments are also described.

17 Claims, 11 Drawing Sheets

|   | R   | R'   | R"   |
|---|-----|------|------|
| 1 | Glc | OH   | H    |
| 2 | Glc | OH   | OH   |
| 3 | Gal | OH   | H    |
| 4 | Gal | H    | H    |
| 5 | H   | OH   | H    |
| 6 | H   | OH   | OH   |
| 7 | H   | H    | H    |
| 8 | H   | OCH$_3$ | OCH$_3$ |
| 9 | H   | OCH$_3$ | OH   |

| 10 | R' | R'' |
|----|-----|-----|
| 11 | OH | H |
| 12 | H | H |
| 13 | OH | OH |

14

15

METHODS AND COMPOSITIONS FOR THE TREATMENT OF OBESITY, INSULIN RELATED DISEASES AND HYPERCHOLESTEROLEMIA

CROSS-REFERENCE TO RELATED APPLICATIONS

This application relies for priority on Provisional Patent Application Ser. No. 60/591,806, filed Jul. 29, 2004.

GOVERNMENT RIGHTS

This invention was funded under USDA Grant No. 2003-35504-13618. The U.S. Government has certain rights to this invention.

BACKGROUND OF THE INVENTION (1) Field of the Invention

The present invention relates to the treatment of insulin related diseases, obesity, diabetes mellitus, hyperglycemia, lipid disorders, hyperlipidemia, or low HDL, hypercholesterolemia, hyperglyceridemia, dyslipidemia, and atherosclerosis. The present invention particularly relates to a method which uses anthocyanins, anthocyanidins, ursolic acid and betulinic acid. The invention particularly relates to Cornus spp. fruit extracts as well as other fruits containing these compounds, such as cherries and berries, or mixtures thereof to increase insulin production by cells in vivo. The present invention also particularly relates to compositions to be used in the method for producing the increase in production of the insulin in vivo in the treatment of the related diseases. The present invention also particularly relates to compositions used to prevent obesity and lowering cholesterol and body weight.

(2) Description of the Related Art

The function of insulin is to maintain normal blood glucose levels either by suppression of glucose output from liver or by the stimulation of glucose uptake and its metabolism (Ross, S. A.; Gulve, E. A.; Wang, M. Chemistry and Biochemistry of diabetes. Chem. Rev. 2004, 104, 1255-1282). Insufficient release of insulin or loss of insulin action at target tissues causes aberrant glucose and lipid metabolism. This results in elevated glucose levels in the blood, a hallmark of diabetes (Jovanovic, L.; Gondos, B. Type-2 diabetes: The epidemic of new millennium. Ann. Clin. Lab. Sci. 1999, 29, 33-42). There are two types of diabetes, type-1 (insulin-dependent diabetes) and type-2 diabetes (non-insulin-dependent diabetes). Type-1 diabetes results from autoimmune destruction or inhibition of pancreatic β-cells, the cells that secrete insulin, which leads into insulin insufficiency. Type-2 diabetes is more prevalent and is caused by the inability of β-cells to secrete sufficient amounts of insulin to overcome insulin resistance established by genetic and environmental factors (Henquin, J. C. Triggering and amplifying pathways of regulation of insulin secretion by glucose. Diabetes 2000, 49, 1751-1760). The insulin resistance is a disorder in which insulin inadequately stimulates glucose transport in skeletal muscle and fat and inadequately suppresses hepatic glucose production. The mechanisms involved that prevent the β-cell from secreting sufficient amounts of insulin to overcome peripheral insulin resistance remain to be established.

Oral hypoglycemic agents that directly stimulate insulin release from β-cells (e.g. sulfonylurea based drugs as exemplified by U.S. Pat. No. 6,852,738 to Jones et al, incorporated herein by reference), however, have shown that insulin secretion from islets of type-2 diabetic patients can be elevated sufficiently to overcome peripheral insulin resistance and normalize blood glucose levels. One of the disadvantages of using sulfonylurea-based drugs is that they fail to control normal blood glucose levels (Pfeiffer, A. F. H. Oral hypoglycemic agents: Sulfonylureas and meglitinides. In B. J. Goldstein, D. Müller-Wieland (Eds.), Text book of Type-2 Diabetes. Martin Dunitz Ltd., London, 2003, pp. 77-85). These drugs also adversely affect the ability of β-cells to secrete insulin and cause weight gain (Pfeiffer, A. F. H. Oral hypoglycemic agents: Sulfonylureas and meglitinides. In B. J. Goldstein, D. Müller-Wieland (Eds.), Text book of Type-2 Diabetes. Martin Dunitz Ltd., London, 2003, pp. 77-85). Hence, there is a role for dietary constituents that can regulate blood glucose level or induce insulin production by pancreatic β-cell in addition to traditional ethical drug treatment.

Reports indicate that consumption of fruits and vegetables, especially rich in polyphenols, decreased the incidence of type-2 diabetes (Anderson, R. A.; Polansky, M. M., Tea Enhanced Insulin Activity. J. Agric. Food Chem. 2002, 50, 7182-7186; Anderson, R. A.; Broadhurst, C. L.; Polansky, M. M.; Schmidt, W. F.; Khan, A.; Flanagan, V. P.; Schoene, N. W.; Graves, D. J. Isolation and Characterization of Polyphenol Type-A Polymers from Cinnamon with Insulin-like Biological Activity. J. Agric. Food Chem. 2004, 52, 65-70; Landrault, N.; Poucheret, P.; Azay, J.; Krosniak, M.; Gasc, F.; Jenin, C.; Cros, G.; Teissedre, P. Effect of a Polyphenols-Enriched Chardonnay White Wine in Diabetic Rats. J. Agric. Food Chem. 2003, 51, 311-318). Also, it is known that dietary antioxidants protect pancreatic β-cells from glucose-induced oxidative stress. Anthocyanins are abundant in fruits, vegetables and processed food products such as wine, cider and tea. However, little is known of its ability to reduce or prevent diabetes.

Also, anthocyanins are nontoxic and reported to possess antioxidant, anti-inflammatory and anticancer activities (Wang, H., Nair, M. G., Strasburg, G. M., Chang, Y., Booren, A. M. Gray, J. I., and DeWitt, D. L. (1999) Antioxidant and anti-inflammatory activities of anthocyanins and their aglycon, cyanidin, from tart cherries. J. Nat. Prod. 62, 294-296; Tall, J. M., Seeram, N. P., Zhao, C., Nair, M. G., Meyer, R. A., and Raja, S. N. (2004) Tart cherry anthocyanins suppress inflammation-induced pain behavior in rat. Behav. Brain Res. 153, 181-188; Kang, S., Seeram, N. P., Nair, M. G., and Bourquin, L. D. (2003) Tart cherry anthocyanins inhibit tumor development in ApcMin mice and reduce proliferation of human colon cancer cells. Canc. Lett. 194, 13-19; Zhang, Y., Vareed, S. K., and Nair, M. G. (2005) Human tumor cell growth inhibition by nontoxic anthocyanidins, the pigments in fruits and vegetables. Life Sci. 76, 1465-1472.).

The bioactive natural products present in vegetables, fruits and herbs have generated considerable interest in prevention and treatment of human degenerative disorders like cancer, diabetes and cardiovascular diseases. For example, nuts, whole grains, fruits, and vegetables are rich source of antioxidants such as polyphenols, terpenoids and pigments and these compounds have been associated with the amelioration of several disease conditions. Similarly, phytochemicals present in garlic, soybeans, cabbage, ginger, licorice, and the umbelliferous vegetables are known to possess anticancer activity (Rui, H. L. (2004) Potential synergy of phytochemicals in cancer prevention: mechanism of action. J. Nutr. 134, 3479S-3485S). Also, the polyphenols present in tea are reported to possess anti-diabetic properties (Vanessa, C., and Gary, W. (2004) A review of the health effects of green tea catechins in in vivo animal models. J. Nutr. 134, 3431S-3440S and Mary E. W., Xiaohui, L. W., Brian, K. L., Robert K. H., Masao, N., and Daryl K. G. (2002) Epigallocatechin gallate, a constituent of green tea, represses hepatic glucose production. *J. Biol. Chem.* 277, 34933-34940.).

The consumption of a diet low in fat and rich in antioxidants reduces the risk of obesity and insulin resistance (Blakely, S.; Herbert, A.; Collins, M.; Jenkins, M.; Mitchell, G.; Grundel, E.; O'Neill, K. R.; Khachik, F. Lutein interacts with ascorbic acid more frequently than with α-tocopherol to alter biomarkers of oxidative stress in female Zucker obese rats. *J. Nutr.* 2003, 133, 2838-2844).

Anthocyanins belong to antioxidant polyphenols and are present in various foods and beverages. Consumption of anthocyanins is associated with reduced risk of several degenerative diseases such as atherosclerosis, cardiovascular disease, cancer and diabetes (Jayaprakasam, B.; Strasburg, G. A.; Nair, M. G. Potent lipid peroxidation inhibitors from *Withania somnifera*. *Tetrahedron* 2004, 60, 3109-3121). These compounds are well-known free radical scavengers and reported as potential chemopreventive agents (Duthie, G. G.; Duthie, S. J.; Kyle, J. A. M. Plant polyphenols in cancer and heart disease: implications as nutritional antioxidants. *Nutr. Res. Rev.* 2000, 13, 79-106). For example, serum antioxidant capacity was increased by the consumption of strawberries, cherries, and red wine (Kang, S. Y.; Seeram, N. P.; Nair, M. G.; Bourquin, L. D. Tart cherry anthocyanins inhibit tumor development in ApcMin mice and reduce proliferation of human colon cancer cells. *Canc. Lett.* 2003, 194, 13-19; Van Velden, D. P.; Mansvelt, E. P. G.; Fourie, E.; Rossouw, M.; Marais, A. D. The cardioprotective effect of wine on human blood chemistry. *Ann. New York Acad. Sci.* 2002, 957, 337-340; Wang, H.; Nair, M. G.; Strasburg, G. M.; Chang, Y. C.; Booren, A. M.; Gray, I. J.; DeWitt, D. L. Antioxidant and anti-inflammatory activities of anthocyanins and their aglycone, cyanidin, from tart cherries. *J. Nat. Prod.* 1999, 62, 294-296). Recent studies demonstrated that the anthocyanin, cyanidin 3-glucoside, reduced the high fat diet induced obesity in mice (Espin, J. C.; Soler-Rivas, C.; Wichers, H. J.; Garcia-Viguera, C. Anthocyanin-based natural colorants. A new source of antiradical activity for foodstuff. *J. Agri. Food Chem.* 2000, 48, 1588-1592). Therefore, the natural colorants present in the food have attracted consumers due to their safety, nutritional and therapeutic values (Millspaugh, C. F. In *American Medicinal Plants*; Dover Publications: New York, 1974; p 282). Since anthocyanins are widely consumed, additional biological activities of these compounds are of great interest.

Several studies suggest that diets rich in fat and low in fiber result in obesity. Obesity alters the lipid metabolism, which in turn leads to insulin resistance. Under obese conditions, the adipose tissue produces an enormous amount of free fatty acids (FFA). The FFA then inhibits the glucose uptake, glycogen synthesis and glucose oxidation (Saltiel, A. R. and Kahn, C. R. (2001) Insulin signaling and the regulation of glucose and lipid metabolism. *Nature* 414, 799-806) and results in hyperglycemia and type-2 diabetes. The type-2 diabetes is an increasingly common disorder and approximately 150 to 300 million people suffer worldwide and expected to double in the next 25 years (King, H., Aubert, R. E., and Herman, W. H. (1998) Global burden of diabetes, 1995-2025: prevalence, numerical estimates, and projections. *Diabetes Care* 21, 1414-1431). Recently, much attention has been focused on food that may be beneficial in preventing diet-induced body fat accumulation and possibly reduce the risk of diabetes and heart disease.

There are several biochemical processes involved in controlling the food intake. The glucagons-like-peptide-1 and -2 (GLP-1 & -2) were synthesized in endocrine cells and released into the blood in response to nutrients intake. The GLP-2 enhances the nutrient absorption by expanding the mucosal epithelium (Ahren, B. (1998) Glucagon-like peptide-1 (GLP-1): a gut hormone of potential interest in the treatment of diabetes. *BioEssays* 20, 642-651 and Drucker, D. J. (2002) Biological action and therapeutic potential of glucagons like peptides. *Gastroenterology* 122, 531-544). The GLP-1 is mainly expressed in gut L-cells and it inhibits glucagon secretion and gastric emptying by the liver, which in turn inhibit the food intake and stimulates insulin biosynthesis and secretion by pancreatic β-cells (Ahren, B. (1998) Glucagon-like peptide-1 (GLP-1): a gut hormone of potential interest in the treatment of diabetes. *BioEssays* 20, 642-651 and Drucker, D. J. (2002) Biological action and therapeutic potential of glucagons like peptides. *Gastroenterology* 122, 531-544). The primary function of pancreatic β-cells is to secrete the bioactive insulin, in response to nutrients, hormones and nervous stimuli, in order to keep the normal physiological glucose concentrations of the body (Rohit, N. K. (2004) The islet β-cell. *The Int. J. Biochem. Cell Biol.* 36, 365-371). The progressive loss of the pancreatic β-cell function in response to elevated blood glucose levels causes the insulin deficiency, which leads to type-2 diabetes. The insulin resistance, the failure of liver, muscle, and adipose tissue to respond to physiologic doses of insulin, also causes type-2 diabetes (Pinget, M., and Boullu-Sanchis, S. (2002) Physiological basis of insulin secretion abnormalities. *Diabet. Met.* 28 (6, Suppl.), 4S21-4S32). Both insulin deficiency and resistance lead to health problems such as hyperlipidemia, atherosclerosis and hypertension (Saltiel, A. R. and Kahn, C. R. (2001) Insulin signaling and the regulation of glucose and lipid metabolism. *Nature* 414, 799-806) and often linked to the impaired carbohydrate and lipid metabolism (Brosche, T. (2001) Plasmalogen levels in serum from patients with impaired carbohydrate or lipid metabolism and in elderly subjects with normal metabolic values. *Arch. Gerontol. Geriatrics* 32, 283-294). These control systems interact in complex pathways and any alteration by genetic, environmental and social factors causes obesity and diabetes (Ross, S. A., Gulve, E. A., and Wang, M. (2004) Chemistry and biochemistry of type 2 diabetes. *Chem. Rev.* 104, 1255-1282). However, some of the complications resulting from social and environmental factors may be delayed or prevented by exercise and proper diet (Christian, K. R., and Barnard, R. J. (2005) Effects of exercise and diet on chronic disease. *J. Appl. Physiol.* 98, 3-30). Epidemiological studies showed that diets rich in fruits and vegetables reduce the incidence of cancer, cardiovascular disease, diabetes, cataracts, and inflammatory disease (World Cancer Research Fund/American Institute for Cancer Research (1997) Food, nutrition and the prevention of cancer: A global perspective 1997, American Institute for Cancer Research Washington, D.C.; U.S. Department of Agriculture, U.S. Department of Health and Human Services (1995) Nutrition and Your Health: Dietary Guidelines for Americans 1995, U.S. Government Printing Office Washington, D.C.; American Heart Association (1996) Dietary guidelines for healthy American adults: A statement for health professionals from the nutrition committee, American Heart Association. *Circulation* 94, 1795-1800; American Cancer Society (1996) Guidelines on diet, nutrition, and cancer prevention: reducing the risk of cancer with healthy food choices and physical activity. *Cancer J. Clin.* 46, 325-341; World Health Organization (1990) Diet, Nutrition and the prevention of chronic diseases: Report of a WHO study group, Technical Report Series 797, WHO Geneva, Switzerland; Willett, W. C. (1999) Goals for nutrition in the year 2000.

*Cancer J. Clin.* 49, 331-352 and Willett, W. C. (1998) Nutritional Epidemiology 1998, Press: Oxford University, New York, N.Y., USA).

Recently, there has been an increased interest in natural hypoglycemic compounds derived from generally regarded as safe (GRAS) plants, fruits and vegetables since they are considered to be less toxic with fewer side effects. These bioactive compounds present in the food can alter gene expression and cellular events (Milner, J. A. (2004) Molecular targets for bioactive food components. *J. Nutr.* 134, 2492S-2498S) resulting in the modification of proteins and their functions. Although several studies suggested that the phytochemicals present in the fruits and vegetables are beneficial to ameliorate adverse health risks, their anecdotal protective effects have not been well understood.

The *Cornus* fruits are used in anti-diabetic traditional Chinese prescription medicines such as "Hachimi-Gan" (Yamahara, J.; Mibu, H.; Sawada, T.; Fujimura, H.; Takino, S.; Yoshikawa, M.; Kitagawa, I. Biologically active principles of crude drugs. Anti-diabetic principles of corni fructus in experimental diabetes induced by streptozotocin. *Yakugaku Zasshi* 1981, 101, 86-90). We have recently reported the quantification of anthocyanins in *Cornus* spp. fruits (Seeram, N. P.; Schutzki, R.; Chandra, A.; Nair, M. G. Characterization, Quantification, and Bioactivities of Anthocyanins in *Cornus* Species. *J. Agri. Food Chem.* 2002, 50, 2519-2523).

The fruits of the *Cornus* species are a rich source of anthocyanins. The fruits of *Cornus mas* L., also known as the European and Asiatic Cornelian cherry, are used in the preparation of beverages in Europe (Kim, D. K.; Kwak, J. H. A Furan derivative from *Cornus officinalis*. *Arch. Pharm. Res.* 1998, 21, 787-789). In traditional medicine, *Cornus officinalis* fruits are known for their analgesic and diuretic activities (Yamahara, J.; Mibu, H.; Sawada, T.; Fujimura, H.; Takino, S.; Yoshikawa, M.; Kitagawa, I. Biologically active principles of crude drugs. Anti-diabetic principles of corni fructus in experimental diabetes induced by streptozotocin. *Yakugaku Zasshi* 1981, 101, 86-90). The *Cornus* fruits are also one of the major constituents of several anti-diabetic herbal preparations in Asian countries (Seeram, N. P.; Schutzki, R.; Chandra, A.; Nair, M. G. Characterization, Quantification, and Bioactivities of Anthocyanins in *Cornus* Species. *J. Agri. Food Chem.* 2002, 50, 2519-2523). Earlier investigation of the fruits of *C. mas* and *C. officinalis* revealed that both contained high levels of anthocyanins (Beckwith, A. G.; Zhang, Y.; Seeram, N. P.; Cameron, A. C.; Nair, M. G. Relationship of Light Quantity and Anthocyanin Production in *Pennisetum setaceum* Cvs. Rubrum and Red Riding Hood. *J. Agric. Food Chem.* 2004, 52, 456-461).

The *C. mas* plant yields fruits similar to tart cherry (*P. cerasus*). It belongs to the family Cornaceae and is a deciduous tree native to Europe and western Asia (Millspaugh, C. F. *American Medicinal Plants*; Dover Publications: New York, 1974; p 282). The fruits of this species have been used in Turkey to make several concoctions. Earlier studies demonstrated that the alcoholic extract of *Cornus officinalis* increased the GLUT 4 mRNA expression, a glucose transporter, in non-insulin dependent diabetes mellitus (NIDDM) rats (Qian, D., Zhu, Y., and Zhu, Q. (2001) Effect of alcohol extract of *Cornus officinalis* Sieb. et Zucc on GLUT4 expression in skeletal muscle in type 2 (non-insulin-dependent) diabetes mellitus rats. *Zhongguo Zhongyao Zazhi* 26, 859-862). The *Cornus* fruits are well known in the Chinese medicine as well and the fruits of this species are used to cure diabetes in China. However, the active compounds that are responsible for the anti-diabetic activity have not been characterized. Earlier studies on fruits from several *Cornus* spp. grown in Michigan revealed that *C. mas* contained high levels of anthocyanins (Seeram, N. P., Schutzki, R., Chandra, A., and Nair, M. G. (2002) Characterization, quantification, and bioactivities of anthocyanins in *Cornus* species. *J. Agric. Food Chem.* 50, 2519-2523).

OBJECTS

It is an object of the present invention to provide compositions and methods which are useful in the treatment of disorders related to insulin production, high cholesterol and body weight. In particular it is an object of the present invention to provide a method and compositions for increasing insulin production in vivo. Further objects will become apparent from the following description and the drawings.

SUMMARY OF THE INVENTION

The present invention relates to a method for controlling obesity in a mammalian patient in need of such treatment which comprises administering to the patient a therapeutically effective amount of composition comprising a compound selected from the group consisting of an anthocyanin, an anthocyanidin, ursolic acid, betulinic acid, and mixtures thereof. The present invention particularly relates to supplement from *Cornus* and other fruits which is substantially free of acids and sugars naturally present in the fruits.

The present invention also relates to a method for treating obesity in a human patient who is diabetic and being treated with a prescription drug for the diabetes which comprises administering to the patient an effective amount of a composition comprising a compound selected from the group consisting of an anthocyanin, an anthocyanidin, ursolic acid, betulinic acid, and mixtures thereof in conjunction with the prescription drug. Preferably the composition is a supplement or pharmaceutical formulation.

Preferably the anthocyanin, anthocyanidin, ursolic acid or betulinic acid are isolated from fruits, vegetables and flowers. Preferably the anthocyanin is selected from the group consisting of cyanidin-3-glycoside, delphindin-3-glycoside, pelargonidin-3-glycoside and mixtures thereof. A "glycoside" is any compound that contains a carbohydrate molecule (sugar), particularly any such natural product in plants, convertible, by hydrolytic cleavage, into sugar and a nonsugar component (aglycone), and named specifically for the sugar contained, as glucoside (glucose), pentoside (pentose), fructoside (fructose), etc. Preferably the anthocyanin, ursolic acid or betulinic acid are isolated from *Cornus mas*. Preferably the anthocyanidin, or anthocyanin, anthocyanidin, ursolic acid, betulinic acid or mixtures thereof are isolated and purified.

The present invention also relates to a method for the treatment of diabetes mellitus in a mammalian patient in need of such treatment for controlling the diabetes mellitus which comprises administering to said patient a therapeutically effective amount of a composition comprising a compound selected from the group consisting of an anthocyanin, an anthocyanidin, ursolic acid, betulinic acid or mixtures thereof.

Preferably the anthocyanin, ursolic acid or betulinic acid are isolated from fruits, vegetables and flowers. Preferably the anthocyanin is selected from the group consisting of cyanidin-3-glycoside, delphinidin-3-glycoside, pelargonidin-3-glycoside and mixtures thereof. Preferably the anthocyanin, ursolic acid, or betulinic acid are isolated from *Cornus mas*. However, anthocyanins can be from other fruits such as cherries and berries.

The present invention also relates to a method for treating or controlling hyperglycemia in a mammalian patient in need of such treatment which comprises administering a therapeutically effective amount of a composition comprising a compound selected from the group consisting of an anthocyanin, ursolic acid, betulinic acid and mixtures thereof, particularly as a supplement.

Preferably the anthocyanin, anthocyanidin, ursolic acid or betulinic acid are isolated from fruits, vegetables and flowers. Preferably the anthocyanin is selected from the group consisting of cyanidin-3-glycoside, delphinidin-3-glycoside, pelargonidin-3-glycoside and mixtures thereof. Preferably the anthocyanin, ursolic acid or betulinic acid are isolated from *Cornus mas*. Preferably the anthocyanidin, anthocyanin, ursolic acid, betulinic acid or mixtures thereof are isolated and purified.

The present invention also relates to a composition for use in treatment of obesity, diabetes, or hyperglycemia as a disease which comprises: an anthocyanin, anthocyanidin, ursolic acid or betulinic acid or mixtures thereof in a daily dosage unit for treatment of the disease over a period of time; and a pharmaceutical carrier.

Most preferably the anthocyanin is selected from the group consisting of cyanidin-3-glucoside, delphinidin-3-glucoside, pelargonidin-3-glucoside and mixtures thereof. Preferably the anthocyanin, anthocyanidin, ursolic acid or betulinic acid are isolated from fruits, vegetables or flowers. Preferably the anthocyanin, ursolic acid or betulinic acid are isolated from *Cornus mas*.

The present invention also relates to a method for treating or controlling lipid disorders, hyperlipidemia, or low HDL in a mammalian patient in need thereof which comprises administering to said patient a therapeutically effective amount of a composition comprising a compound consisting of an anthocyanin, anthocyanidin, ursolic acid, betulinic acid, or mixtures thereof, particularly as a supplement.

The present invention also relates to a method for treating or controlling hypercholesterolemia in a mammalian patient in need of such treatment which comprises administering to said patient a therapeutically effective amount of a composition comprising a compound consisting of an isolated anthocyanin, anthocyanidin, ursolic acid, betulinic acid, or mixtures thereof, particularly as a supplement.

The present invention also relates to a method for treating or controlling hyperglyceridemia in a mammalian patient in need of such treatment which comprises administering to said patient a therapeutically effective amount of a composition comprising a compound selected from the group consisting of an isolated anthocyanin, anthocyanidin, ursolic acid, betulinic acid, or mixtures thereof, particularly as a supplement.

The present invention also relates to a method for treating or controlling dyslipidemia and/or low HDL cholesterol in a mammalian patient in need of such treatment which comprises administering to said patient a therapeutically effective amount of a composition comprising a compound selected from the group consisting of an isolated anthocyanin, anthocyanidin, ursolic acid, betulinic acid, or mixtures thereof, particularly as a supplement.

The present invention also relates to a method for treatment of atherosclerosis in a mammalian patient in need of such treatment which comprises administering to said patient a therapeutically effective amount of a composition comprising a compound selected from the group consisting of an isolated anthocyanin, anthocyanidin, ursolic acid, betulinic acid, or mixtures thereof, particularly as a supplement.

Most preferably the compound is from *Cornus mas*. Preferably the anthocyanin, anthocyanidin, ursolic acid, betulinic acid or mixtures thereof are isolated and purified from this or other fruits.

Metabolites of the compounds of this invention that are therapeutically active are within the scope of the claimed parent compounds. Prodrugs, which are compounds that are converted to the claimed compounds as they are being administered to a patient or after they have been administered to a patient, are also within the scope of the claimed active compounds.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing obesity, diabetes mellitus and/or hyperglycemia or hypertriglyceridemia or other diseases, generally satisfactory results are obtained when the compounds of the present invention are administrated at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligram to about 50 milligrams. In the case of a 70 kg adult human, the total daily dose will generally be from about 7 milligrams to about 350 milligrams. This dosage regimen may be adjusted to provide the optimal therapeutic response.

Another aspect of the present invention provides pharmaceutical compositions and a pharmaceutically acceptable carrier. The pharmaceutical compositions of the present invention comprise the claimed compounds or pharmaceutically acceptable salt or prodrug thereof as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions, or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their case of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as maltodextrin, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds can also be administered parenterally. Solutions or suspensions of these active compounds can be prepared in water suitably mixed with a surfactant such as hydroxyl-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exits. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Compounds can be used in combination with other drugs that may also be useful in the treatment, prevention, suppression or amelioration of the diseases or conditions. Such other drugs may be administered, by a route and in an amount commonly used therefor, contemporaneously or sequentially with a compound. When a compound is used contemporaneously with one or more other drugs, a pharmaceutical composition in unit dosage form containing such other drugs and the compound is preferred. However, the combination therapy also includes therapies in which the compound of Formula I and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound.

DESCRIPTION OF THE PREFERRED EMBODIMENTS

Figure 1:
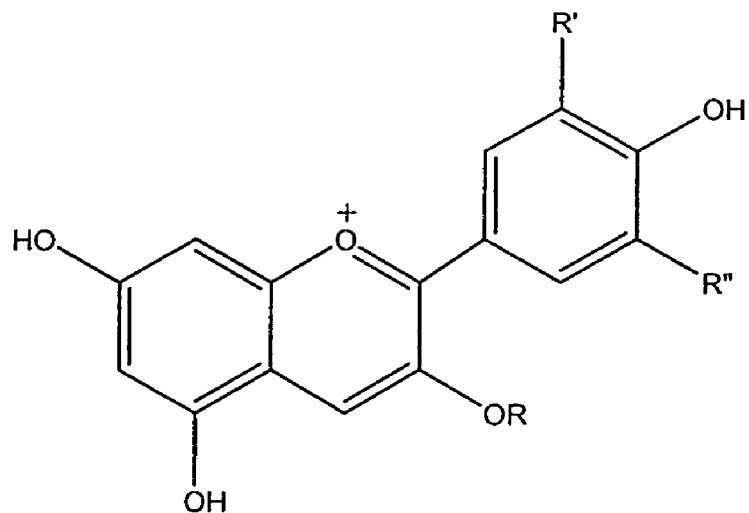
FIG. 1 is a drawing showing structures of anthocyanins 1-4 and anthocyanidins 5-9.

The present discloses and demonstrates the ability of anthocyanins, cyanidin-3-glucoside, delphinidin-3-glucoside, cyanidin-3-galactoside, and pelargonidin-3-galactoside; and anthocyanidins, cyanidin, delphinidin, pelargonidin, malvidin, and petunidin to stimulate insulin secretion by rodent pancreatic beta cells (INS-1 813/32) in vitro. The compounds were tested in the presence of 4 and 10 mM glucose concentrations. Cyanidin-3-glucoside and delphinidin-3-glucoside were the most effective insulin secretagogues among the anthocyanins and anthocyanidins tested at 4 and 10 mM glucose concentrations. Pelargonidin-3-galactoside is one of the major anthocyanins and its aglycone, pelargonidin, caused a 1.4-fold increase in insulin secretion at 4 mM glucose concentration. Remaining of the anthocyanins and anthocyanidins tested had only marginal affects on insulin at 4 and 10 mM glucose concentrations.

Examples of Insulin Stimulation

Materials and Methods

Chemicals. Fetal bovine serum (FBS) and RPMI-1640 medium were obtained from Invitrogen (Grand Island, N.Y.). All organic solvents used were ACS reagent grade. HEPES, penicillin-streptomycin, glutamine, sodium pyruvate, 2-mercaptoethanol, trypsin-EDTA, BSA (Bovine, Albumin; RIA Grade), Folin-Ciolatues reagent and chemicals used for the preparation of buffers were purchased from Sigma-Aldrich Chemical Co. (St. Louis, Mo.). The anthocyanidins, cyanidin, delphinidin, pelargonidin, malvidin, and petunidin, used in the assay were purchased from Chromadex (Laguna Hills, Calif.).

Anthocyanins. Delphinidin-3-glucoside was purified from *C. officinalis* fruits. Cyanidin-3-galactoside and pelargonidin-3-galactoside were isolated from *C. mas* fruits. Pure cyanidin-3-glucoside used in this study was from our storage at −20° C.

Isolation and purification of anthocyanins. The *Cornus* fruits were blended with water (pH=3) and filtered. The filtrate was passed through XAD-16 AMBERLITE resin in a column and the resin with the adsorbed anthocyanins was washed repeatedly with water. The XAD-16 resin was then eluted with acidic MeOH (pH=3) and the resulting solution was concentrated under reduced pressure to yield a crude anthocyanin fraction. This fraction was purified by MPLC column ($C_{18}$ silica) using MeOH:$H_2O$ (pH=3) under gradient conditions. The anthocyanins were eluted with MeOH:$H_2O$ (65:35, v/v) solvent system. The purity of the compounds was checked by HPLC (Waters Corp.) using Capcell $C_{18}$ analytical column under gradient conditions. The solvents used were A: TFA:$H_2O$ (99.9:0.1; v/v) and B: $H_2O$:$CH_3CN$:$CH_3COOH$:TFA (50.4:48.5:1.0:0.1; v/v/v/v). The gradient was 20% B to 60% B in 26 min and to 20% B in 30 min at a flow rate of 0.8 ml/min. The peaks were detected at 520 nm using a PDA.

Insulin Secretion Studies. INS-1 832/13 cells (kindly provided by Dr Christopher Newgard, Duke University, N.C.) were routinely cultured in 5% $CO_2$/air at 37° C. in RPMI-1640 medium containing 11.1 mM glucose and supplemented with 10% FBS (Fetal Bovine Serum), 10 mM HEPES, 100 U/ml penicillin, 100 µg/ml streptomycin, 4 mM Glutamine, 1 mM sodium pyruvate, and 50 µM 2-mercaptoethanol. Cells were passed weekly after trypsin-EDTA detachment. For static secretion studies, cells were plated on 24 well plates at a density of $0.64 \times 10^6$ cells per well and grown for 24 h. The cells were then cultured for an additional 24 h in RPMI-1640 containing 4 mM glucose and the supplements described above. Cells were then incubated twice for 30 min in Krebs Ringer Bicarbonate buffer (KRBB) containing 4 mM glucose and 0.1% BSA. Cells were rapidly washed with KRBB and incubated for 60 min KRBB containing 4 or 10 mM glucose with or without the indicated anthocyanins or anthocyanidins. The medium was then removed for determining insulin release. The cells were then washed twice with PBS and dissolved in 1 M NaOH. Cellular protein concentration was then determined by Lowry assay. Anthocyanins and anthocyanidins were dissolved in DMSO to obtain desired concentrations. Final concentration of DMSO was 0.1%. The insulin secreted into the medium by the cells was determined by radioimmuno assay and normalized to total cellular protein.

Radio Immuno Assay (RIA). The Kit for RIA was purchased from LINCO Research Inc. (St Charles, Mo.), and the assay was conducted according to the manufacturer's directions. Briefly, 0.1-10 ng of insulin standards (100 µl) were added to 12×75 mm test tubes. Similarly, samples (25 µl) from the insulin secretion studies were also added to the test tubes. To this, an aliquot (75 µl) of assay buffer was added. The $^{125}$I labeled insulin (100 µl) was then added to each test tube. An aliquot of 100 µL anti rat insulin antibody was added to the tubes, mixed and incubated at 4° C. for 24 h and incubated further with 1 ml aliquot of the precipitating reagent for 20 min at 4° C. to precipitate the insulin bound to the antibody. The tubes were then centrifuged and the radioactivity was measured using a gamma counter.

Lowry protein Assay. The amount of protein in the assay wells was determined by Lowry method. The Lowry assay solution was prepared by combining the Lowry solution, $CuSO_4 \cdot 5H_2O$ (1%), and sodium tartarate (1%). Briefly, the protein sample (100 µl) and Lowry mixture (1 mL) were mixed in a test tube (12×75). The Folin-Ciolatues reagent (100 µl) was added to these tubes, mixed, and incubated for 30 min at room temperature. The optical density of resulting solutions was read at 700 nm using a UV spectrophotometer.

Results and Discussion

The investigation of *Cornus* fruits indicated that the primary bioactive components in them were cyanidin, delphinidin and pelargonidin glycosides. Therefore, the attention was focused on the insulin secreting ability of these anthocyanins and their aglycones using pancreatic beta cells in order to substantiate the anecdotal use of *Cornus* fruits in anti-diabetic preparations. Petunidin, malvidin and peonidin aglycones were included in the assay since they are abundant in other fruits.

Anthocyanins are water-soluble compounds. The aqueous extracts of *C. mas* fruits contained sugars, bioflavonoids and anthocyanins and hence was fractionated by XAD-16 resin. The resulting anthocyanin fraction eluted from the resin was purified by MPLC to afford pure anthocyanins. The glucose-induced insulin production by INS-1 832/13 cells was determined at 4, 10 and 16 mM glucose concentrations and found that the insulin secretion reached a lag phase at 10 mM glucose concentration (data not presented). The glucose concentration at 4 mM level is representative of the normal glucose level in human. The insulin secretion per mg of protein by cells at 10 mM glucose was three fold higher when compared to the insulin secretion at 4 mM glucose concentration.

Figure 2A:
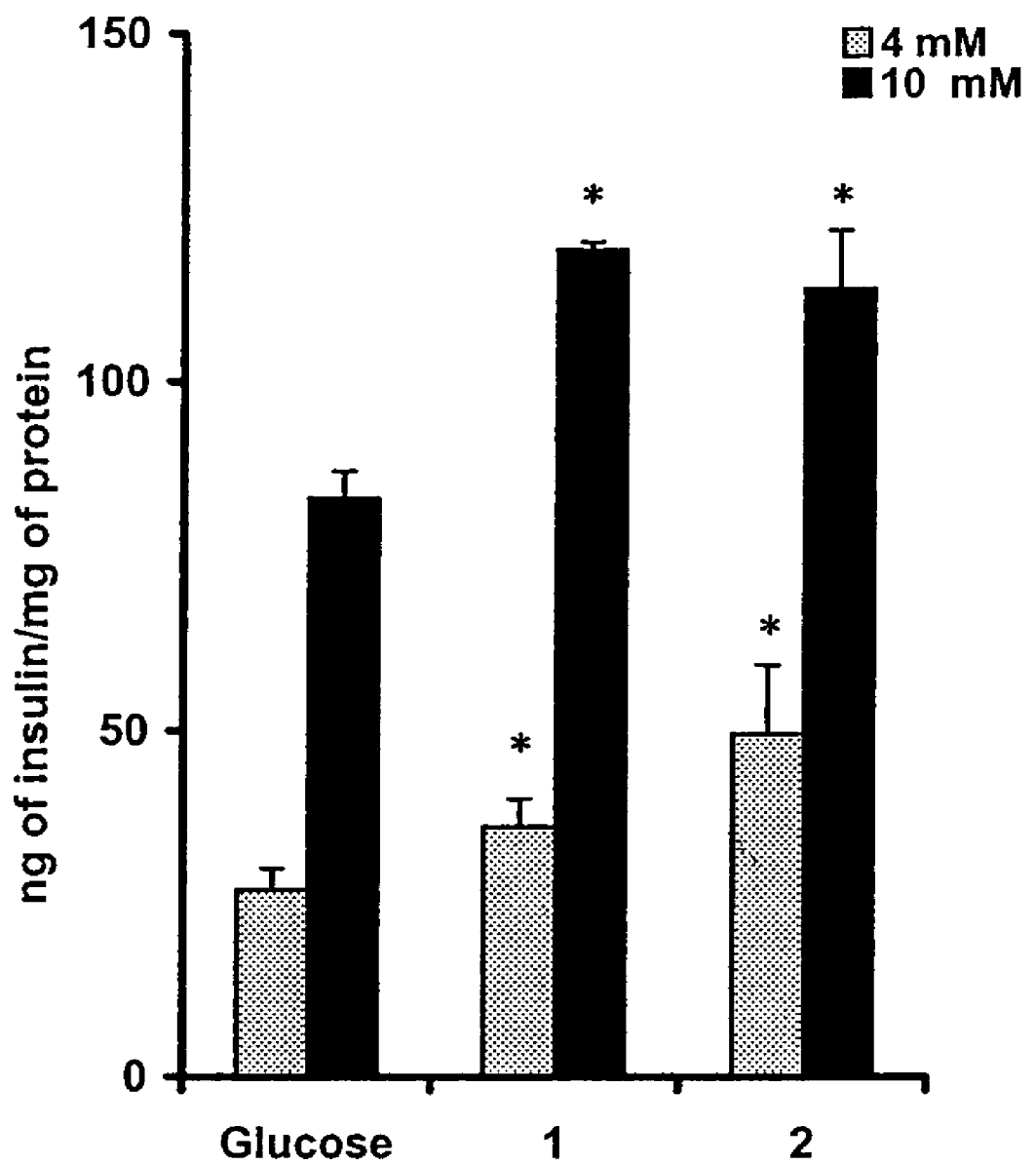
FIG. 2A is a graph showing the amount of insulin secreted per milligram of protein by compounds 1 and 2 and FIG. 2B by compounds 5 and 6 in the presence of 4 and 10 mM glucose. The final DMSO concentration in the assay wells was 0.1%. The results represented are the average of three or five independent experiments and each sample was assayed in duplicate. Insulin secretion by compounds 1, 2, 5 and 6 were significant at * (95% or $p \leq 0.05$) or ** (99% or $p \leq 0.01$) as determined by LSD using the t-test.
Figure 3:
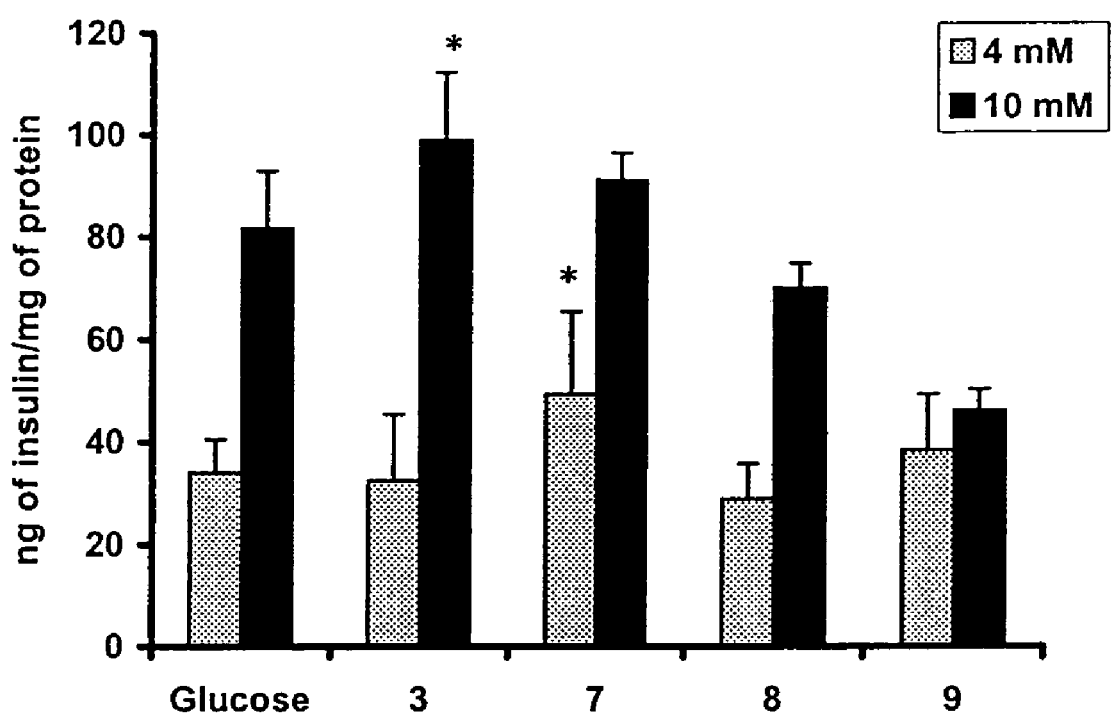
FIG. 3 is a graph showing the insulin secreted by compounds 3, 7-9 at 4 and 10 mM glucose concentrations. The amount of insulin secreted was normalized to milligram protein. The final DMSO concentration in the assay wells was 0.1%. The results represented are the average of three independent experiments and each sample was assayed in duplicate. Insulin secretion by compounds 3, 7-9 was significant at * (95% or $p \leq 0.05$) as determined by LSD using the t-test.

Anthocyanins and anthocyanidins were tested at 4 and 10 mM glucose loads in the cell growth medium. Anthocyanins and anthocyanidins were assayed initially at 50 µg/mL concentration. The anthocyanin, cyanidin 3-glucoside showed an increase in insulin secretion at 4 mM glucose by 9 ng/mg of protein (1.3 fold) whereas it enhanced the insulin secretion by 1.43 fold (119 ng/mg protein) at 10 mM glucose concentration (FIG. 2A). Delphinidin-3-glucoside was the most active anthocyanin tested and showed a 1.8-fold increase (49 ng/mg of protein) in insulin secretion at 4 mM glucose concentration. However, at 10 mM glucose it exhibited only a 1.4-fold (113 ng) increase (FIG. 2A) in insulin production. The insulin secreted by cells at 4 and 10 mM glucose concentrations in this assay were 27 and 83 ng of insulin per mg protein, respectively. The anthocyanins, cyanidin-3-galactoside and pelargonidin-3-galactoside, did not increase the insulin secretion at 4 mM glucose concentration. However, cyanidin-3-galactoside showed an increase of 17 ng/mg of protein of insulin (1.2 fold) at 10 mM glucose concentration (FIG. 3). The pelargonidin-3-galactoside was tested only once due to the limitation of sample.

The anthocyanin cyanidin-3-glucoside was evaluated for dose dependent insulin secretion at 5, 10, 50, 100 and 250 µg/mL concentrations. The glucose concentration used in this assay was 4 mM level which is representative of the normal glucose level in human. At this concentration, untreated cells secreted 33 ng of insulin/mg of protein. The insulin secreted by cyanidin-3-glucoside treated cells was 46 ng of insulin per mg protein at 5 µg/mL. However, there was no significant difference in insulin secretion at 10, 50, 100 and 250 µg/mL concentrations of compound 1. There was not an adequate supply of delphinidin-3-glucoside to conduct dose dependent assays.

Figure 2B:
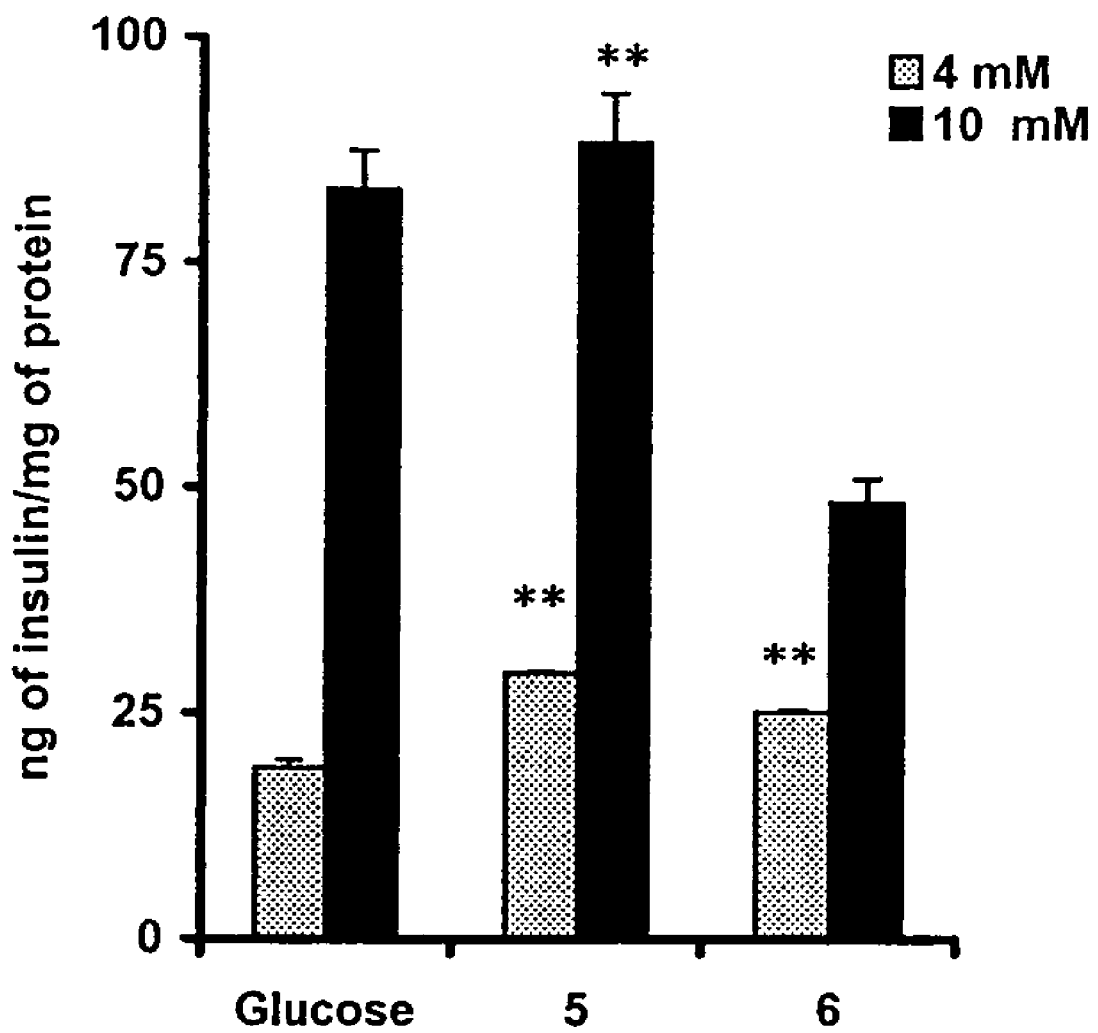

The anthocyanidins were assayed at 50 µg/mL concentration. The aglycone of cyanidin-3-glucoside, cyanidin, enhanced insulin secretion by 1.5 fold (29 ng/mg of protein) at 4 mM glucose whereas at 10 mM glucose it secreted 88 ng/mg of protein (FIG. 2B). The untreated cells at 4 and 10 mM glucose secreted 19 and 83 ng insulin/mg of protein, respectively, in this set of assay. The aglycone delphinidin showed an increase in insulin secretion by 6 ng/mg of protein at 4 mM glucose concentration and was not significant. Delphinidin did not show glucose-induced insulin secretion at 10 mM glucose (FIG. 2B). Pelargonidin was the most active anthocyanidin and it secreted 49 (1.4 fold) and 91 (1.2 fold) ng of insulin/mg of protein at 4 and 10 mM glucose, respectively (FIG. 3). The aglycone petunidin increased insulin secretion by 4 ng of insulin/mg protein at 4 mM glucose concentration. However, malvidin did not show an increase in insulin secretion with respect to the untreated cells.

The results suggested that both anthocyanins and anthocyanidins are insulin secretagogues. The most potent among them was delphinidin-3-glucoside and it significantly induced the insulin secretion at 4 and 10 mM glucose concentrations compared to the untreated cells. Although cyanidin-3-glycoside was less active than delphinidin-3-glucoside at lower glucose concentration, it was more active at higher glucose concentration. Among the galactosides, pelargonidin-3-galactoside did not induce insulin secretion at 4 and 10 mM glucose concentrations studied, whereas cyanidin-3-galactoside showed significant increase in insulin secretion. The ability of anthocyanins studied to secrete insulin was in the increasing order of delphinidin-3-glucoside>cyanidin-3-glucoside>pelargonidin-3-galactoside. This indicated that the number of hydroxyl groups in ring-B of anthocyanins played an important role in their ability to secrete insulin. Among the anthocyanidins tested, pelargonidin was the most active at 4 mM glucose. Other aglycones did not potentiate significant insulin secretion at 4 or 10 mM glucose concentrations studied.

The results suggest that isolated and purified anthocyanins and anthocyanidins from fruits and vegetables are useful to treat diabetes.

Examples of Treatment of Obesity

Anthocyanins (FIG. 9), ursolic and betulinic acids from *C. mas* fruits were purified and evaluated their efficacy by using C57BL/6J transgenic mice as agents to prevent obesity and insulin resistance resulting from the consumption of high fat diet. The mice were fed initially for four weeks with high fat diet and were then switched to high fat diet containing test compounds for another eight weeks. The glucose tolerance test (GTT) revealed that the high fat diet control mice were insulin resistant and the mice treated with anthocyanins and ursolic acid overcame the insulin resistance. The average weight gain of control mice fed with the high fat diet (60% K. Cal.) during the treatment period was 9.76±0.55 g, whereas the mice treated with anthocyanins, betulinic and ursolic acids were 7.41±0.93, 7.73±0.44 and 8.78±0.96 g, respectively. The cholesterol levels of the anthocyanins and betulinic acid treated mice were significantly lower than the control animals. The plasma insulin levels of anthocyanins and betulinic acid treated animals were 567±32.36 and 460.86±93.68 ng/mL, respectively, whereas the animals treated with ursolic acid showed 52.25±8.84 ng/mL of insulin compared to the control animals. This in vivo study confirmed that anthocyanins are excellent insulin secretagogues and may be beneficial in preventing obesity and insulin resistance in addition to lowering the total cholesterol.

Experimental Procedures

Purification of Anthocyanins: Cyanidin galactoside, pelargonidin galactoside and delphinidin galactoside were isolated as a pure mixture of anthocyanins from the *C. mas* fruits as previously disclosed. Briefly, the seeds were separated and the resulting pulp was blended with water (pH=3) and filtered. The filtrate was adsorbed onto XAD-16 AMBERLITE resin and washed repeatedly with water to remove the sugars and other organic acids. The adsorbed anthocyanins were then eluted with acidic MeOH (pH=3). The anthocyanins mixture thus obtained was purified by medium pressure liquid chromatography (MPLC) column ($C_{18}$ silica) using MeOH:$H_2O$ (pH=3) under gradient conditions. The fractions eluted with solvent system MeOH:$H_2O$ (65:35, v/v) were collected and evaporated to dryness under vacuum. The purity of anthocyanins was confirmed by HPLC (Waters Corp.) using Capcell $C_{18}$ analytical column and detected at 520 nm (PDA, Waters Corp.).

Isolation of Betulinic acid: The seeds (700 g) from *C. mas* fruits (5 Kg) were separated, lyophilized and extracted with n-hexane (3×1 L), ethyl acetate (3×1 L), and methanol (3×1 L), successively. The EtOAc extract (3.0 g) was purified by silica gel MPLC under gradient conditions with n-hexane and EtOAc as the mobile phases. The fractions collected from hexane-EtOAc (7:3) elution were evaporated to dryness and crystallization from MeOH gave betulinic acid (2.5 g).

Isolation of Ursolic acid: The lyophilized pulp and skin were extracted with n-hexane (3×1 L), EtOAc (3×1 L) and MeOH (3×1 L) successively. The EtOAc (3.5 g) extract was purified over column chromatography using n-hexane and EtOAc gradients. The hexane-EtOAc (7:3) eluates were evaporated to dryness under vacuum and crystallization of the resulting residue from MeOH yielded ursolic acid (2.2 g). Both ursolic and betulinic acids were characterized by $^1$H and $^{13}$C NMR spectral experiments (Werner, S., Nebojsa, S., Robert, W., Robert, S., and Olaf, K. (2003) Complete assignments of $^1$H and $^{13}$C NMR resonances of oleanolic acid, 18α-oleanolic acid, ursolic acid and their 11-oxo derivatives. *Mag. Res. Chem.* 41, 636-638.).

Animals and Diet: Male C57BL/6J mice, 4 weeks old, were purchased from Jackson Laboratories (Bar Harbor, Me., USA). The mice were individually housed under controlled temperature (70° F.) and 12 h light-dark cycles. The mice (n=40) had free access to water and laboratory non-purified diet for 5 days. After acclimatization, the mice were randomly divided into groups 1-5 (n=8) for the study. The experiments were carried out according to the ethical guidelines of University Laboratory Animal Resources (ULAR) at Michigan State University, East Lansing, Mich. The diets, 10% K. Cal. (normal) and 60% K. Cal. (high fat), were purchased from Research Diets (New Brunswick, N.J.). The composition of the diet is shown in the Table 1.

Table 1. Composition of Normal (105 K. Cal.) and High Fat (60% K. Cal.) Diets

| Ingredients | Normal | High fat |
| --- | --- | --- |
| Casein | 200 | 200 |
| L-Cystein | 3 | 3 |
| Corn Starch | 315 | 0 |
| Maltodextrin | 35 | 125 |
| Sucrose | 350 | 68.8 |
| Cellulose | 50 | 50 |
| Soybean oil | 25 | 25 |
| Lard | 20 | 245 |

The controls were groups 1 and 2 and received normal (10% K. Cal.) and high fat (60% K. Cal.) diets, respectively, throughout the study. The food was prepared for each treatment separately by mixing 1 g of pure anthocyanin mixture, 500 mg each of betulinic and ursolic acids per kilogram high fat diet. The treatment groups, 3-5, were fed initially for 4 weeks with the high fat diet and then switched to the diet containing anthocyanins, betulinic acid or ursolic acids. Food was changed at intervals of three days to avoid oxidation of the fat or compounds. The daily food intake (FIG. 1) and the weekly body weight for each animal were determined throughout the study (FIG. 2A-C).

Collection of serum, liver and adipose tissue. The feeding was terminated after 12 weeks. The animals were then anesthetized by using isoflurane, sacrificed and blood was collected by cardiac puncture in heparinized tubes. The plasma was separated by centrifugation at 1600×g for 10 min at 4° C., frozen immediately and stored at −20° C. until use. The liver and epididymal white adipose tissue (WAT) were collected according to the anatomical landmarks, weighed and immediately frozen under liquid nitrogen. Also, the limb muscles were collected and frozen in liquid nitrogen. The pancreas were collected and stored in optimal cutting temperature (O.C.T) (Sakura Finetek, Inc., CA) and frozen in liquid Nitrogen. All tissues were then transferred from liquid nitrogen and stored at −80° C. until analyses.

Glucose Tolerance Test (GTT). The glucose tolerance test was performed on five animals from each group (n=5) after 6 weeks of supplementation. The blood glucose level was measured at time 0 (min) with a Free Style Flash (TheraSense, Inc., CA) handheld glucometer using the test strips (Free Style, TheraSense, Inc., CA). For GTT, a sterile solution containing 2 g of glucose per kg body weight was injected intraperitoneally (i.p.). The tail vein blood was collected and glucose levels measured at 5, 10, 15, 30, 60, and 90 min, respectively. The blood glucose levels were plotted against the time (FIG. 3).

Radio Immuno Assay (RIA). The plasma insulin levels were measured by rat insulin RIA kit purchased from LINCO Research Inc. (St Charles, Mo.). The insulin standards (100 µl aliquots) were pipetted to 12×75 mm test tubes. A total of 10 concentrations of insulin, ranging from 0.1-10 ng/mL, were used to determine the standard curve. The plasma samples (aliquots of 1-25 µl) were added to test tubes and the assay buffer was added to attain a total sample volume of 100 µl. The $^{125}$I labeled insulin and anti rat insulin antibody (100 µL each) were added to the tubes, mixed and incubated at 4° C. After 24 h, the precipitating reagent (1 mL) was added and incubated again at 4° C. for 20 min to precipitate the insulin bound to the antibody. The tubes were then centrifuged for 20 min at 3000 g, decanted and the radioactivity was measured using a gamma counter.

Determination of Plasma Cholesterol: The total plasma cholesterol was analyzed by Clinical Pathology Laboratory at the Diagnostic Center for Population and Animal Health, College of Veterinary Medicine, Michigan State University according to the established standard analytical protocol for total cholesterol Results and Discusssion

*Cornus mas* fruits, also known as cornelian cherry, are similar to tart cherries (*P. cerasus*). The phytochemical examination of this plant yielded pelargonidin galactoside, cyanidin galactoside, and delphinidin galactoside as the major anthocyanins (Seeram, N. P., Schutzki, R., Chandra, A., and Nair, M. G. (2002) Characterization, quantification, and bioactivities of anthocyanins in *Cornus* species. *J. Agric. Food Chem.* 50, 2519-2523) and triterpenoids such as ursolic and betulinic acids. The transgenic model mouse is regularly employed as a model to study the metabolic and endocrine disorders. The C57BL/6J model mice used were homozygous for a leptin receptor mutation and develop hyperphagia, obesity, hyperinsulinemia and hyperglycemia (Coleman, D. (1978) Obese and diabetes: two mutant genes causing diabetes-obesity syndromes in mice. *Diabetologia* 14, 141-148). Therefore, the mice were fed with the purified anthocyanins, betulinic and ursolic acids from *C. mas* to evaluate their efficacy in the prevention of diet-induced obesity and insulin resistance. The animals were fed on high fat diet for four weeks prior to the treatment of compounds, incorporated in high fat diet, for eight weeks. The control groups of animals received either normal or high fat diets.

Body weight and Food Intake. The food intake for the group-1 animals was around ≅4.5 g for the first three weeks and then decreased to ≅3.5 g per day (FIG. 1) and stayed steady throughout the experiment. The food intake for group-2 animals was steady through out the experiment and was ≅2.8 g per day (FIG. 1). It is evident from the results that test compounds did not affect the food intake of the animals. The amount of food intake by animals in groups 3-5 were also about 2.8 g per day throughout the experiment (FIG. 1).

The body weights of animals in group 1 (normal diet) and 2 (high fat diet) were significantly different with an average weight of 31.5 and 36.91 g, respectively. The animals on high fat diet treated with compounds 1 (group 3), 2 (group 4) and 3 (group 5) weighed 34.19, 33.54 and 34.89 g, respectively (FIGS. 2A-2C). The overall weight gain during the experimental period (12 weeks) for the group-1 and -2 animals were 13.94 and 18.98 g, respectively. Similarly, the group 3, 4, and 5 animals gained 15.91, 15.16 and 17.45 g of bodyweight, respectively. The weight gained by these animals during the treatment period was 7.41, 7.73 and 8.78 g, respectively, whereas the group-1 and -2 controls showed the bodyweight gain of 6.63 and 9.76 g, respectively.

Glucose Tolerance Test. The glucose tolerance test (GTT) was conducted by intraperitoneal (i.p.) injection of the glucose solution (2 g/kg). The blood glucose levels in animals injected with glucose were determined by drawing blood from tail vein at 5, 10, 15, 30, 60 and 90 min intervals. The zero time blood glucose level among the groups were almost identical. The initial glucose levels of low fat and high fat control groups (1 and 2) were 133.8±15.37 and 119.8±7.24 mg/dL, respectively (FIG. 3). The blood glucose level determined in animals treated with compounds 10-13 were 123.4±4.65, 123.4±6.0 and 113.5±15.5.16 mg/dL, respectively. The blood glucose concentration reached the maximum at 30 min after the glucose injection in all groups except for ursolic acid treated animals. Also, the glucose absorption was slow in this group and the blood glucose concentration reached the maximum at 60 min. After 90 min of glucose load, the blood glucose levels of animals fed with normal and high fat diet were 190±6.31 and 363±19.76 mg/dL, respectively. Similarly, the blood glucose levels of animals in groups 3-5 were 221±31.5, 317.8±21.9 and 227±22.982, respectively.

Plasma Insulin Levels: The plasma insulin was measured by using Radio Immuno Assay (RIA) (Qian, D., Zhu, Y., and Zhu, Q. (2001) Effect of alcohol extract of *Cornus officinalis* Sieb. et Zucc on GLUT4 expression in skeletal muscle in type 2 (non-insulin-dependent) diabetes mellitus rats. *Zhongguo Zhongyao Zazhi* 26, 859-862). The insulin levels measured for control animals, groups 1 and 2, were 0.47±0.14 and 0.41±0.1 ng/mL, respectively (FIG. 4), where as the animals treated with the anthocyanins, betulinic and ursolic acids showed 567.98±32.36, 460±93.68 and 52.25±8.84 ng/mL of insulin, respectively.

Fasting Blood Glucose: The fasting blood glucose of the normal and high fat diet controls were measured to determine whether the animals consumed the high fat diet were diabetic or not. The animals were deprived of food for 6 h and the glucose levels were determined from blood collected from the tail vein. The glucose levels of normal (n=8) and high fat diet (n=8) fed animals were 126.6±4.6 and 125±5.19 mg/dL, respectively.

Figure 5A:
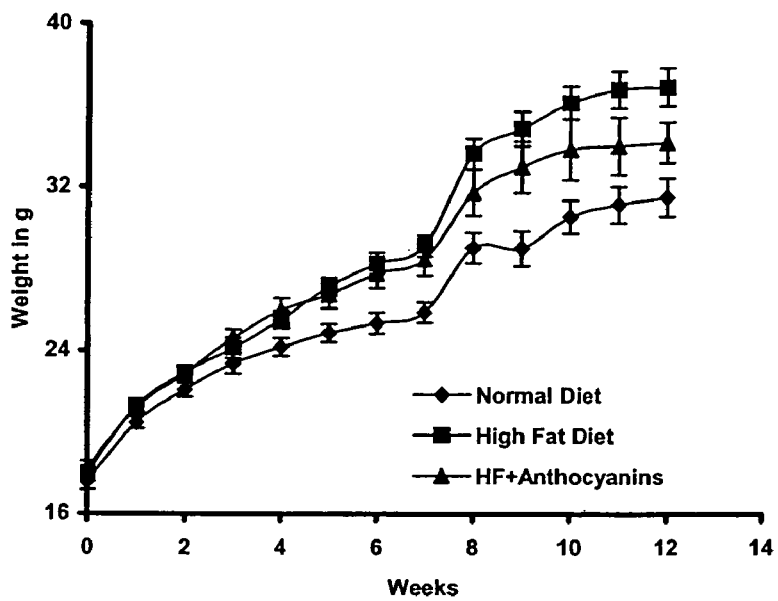
FIGS. 5A, 5B and 5C are graphs showing body weight variation of C57 BL/6J mice in obesity studies during 12 weeks of feeding. The normal and high fat diet controls received 10% and 60% K. Cal., respectively, in their diet throughout the experiment. Anthocyanins, betulinic acid and ursolic acid were separately mixed in high fat diet at 1.0, 0.5 and 0.5 g per Kg of food, respectively. The groups treated with the compounds were initially fed with high fat diet (60% K. Cal.) for four weeks and then were switched to diet containing the appropriate treatment. Data represents mean±SEM, n=8.
Figure 5B:
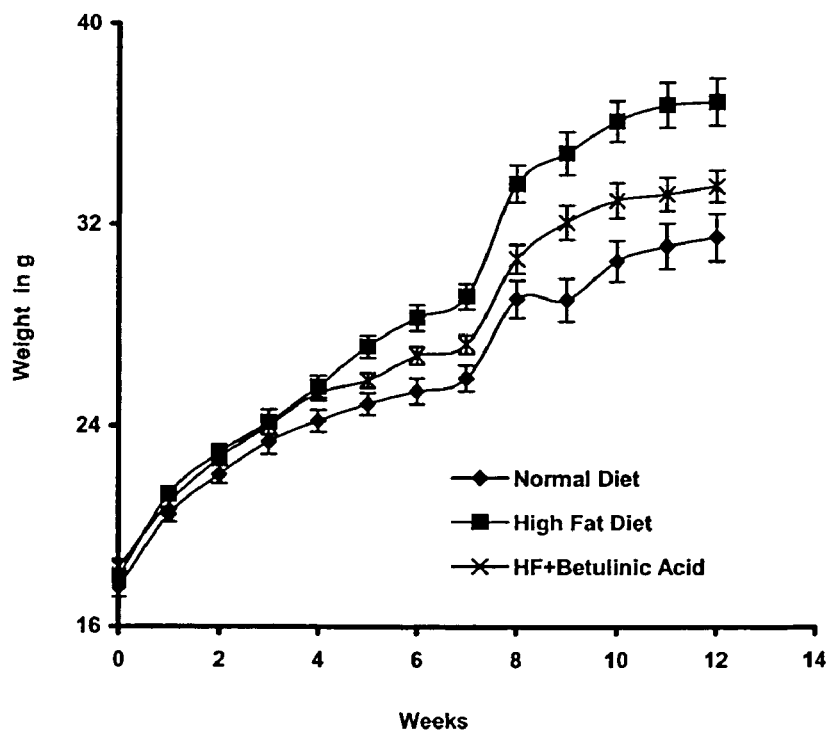
Figure 5C:
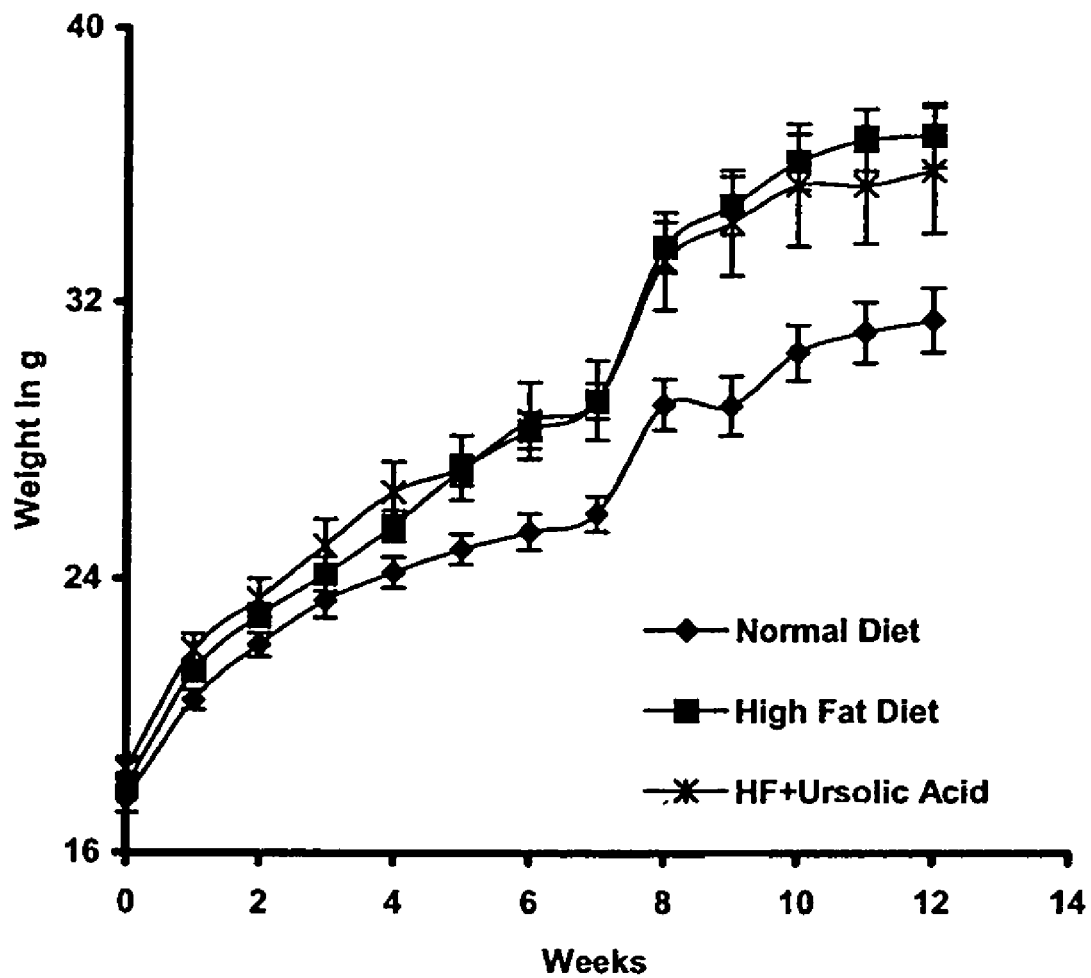

Plasma Cholesterol: The plasma cholesterol levels of the normal and high fat diet controls were 120.5±10.61 and 156.4±8.26 mg/dL, respectively. The cholesterol of the anthocyanins and betulinic acids treated animals was 134.2±15.5 and 126.5±14.01 mg/dL, respectively (FIG. 5).

The food intake of animals on high fat diet alone and high fat diet containing test compounds did not vary over the course of the study. It is interesting to note that the control animals on normal diet consumed more food than the animals on high fat diet. The caloric intake by the high fat diet control and treatment groups was about 14.56 K. Cal. per day whereas the normal diet controls consumed 13.3 K. Cal. per day.

The animals fed on anthocyanin containing diet showed a remarkable decrease in bodyweight as compared to the high fat diet controls. The weight loss observed for anthocyanins and betulinic acid fed animals were 24 and 21%, respectively (FIGS. 5A and 5B). However, the weight loss observed for animals fed on ursolic acid was not significant compared to the high fat diet control. The plasma of anthocyanin and betulinic acid treated animals showed a considerable decrease in total cholesterol compared to the high fat diet control (FIG. 5). The plasma from ursolic acid treated animals was not sufficient enough to complete the total cholesterol assay. The food intake for animals in groups 2-5 was similar throughout the study and hence the weight loss observed for anthocyanins fed animals suggested its potential application in the prevention of obesity.

Figure 6:
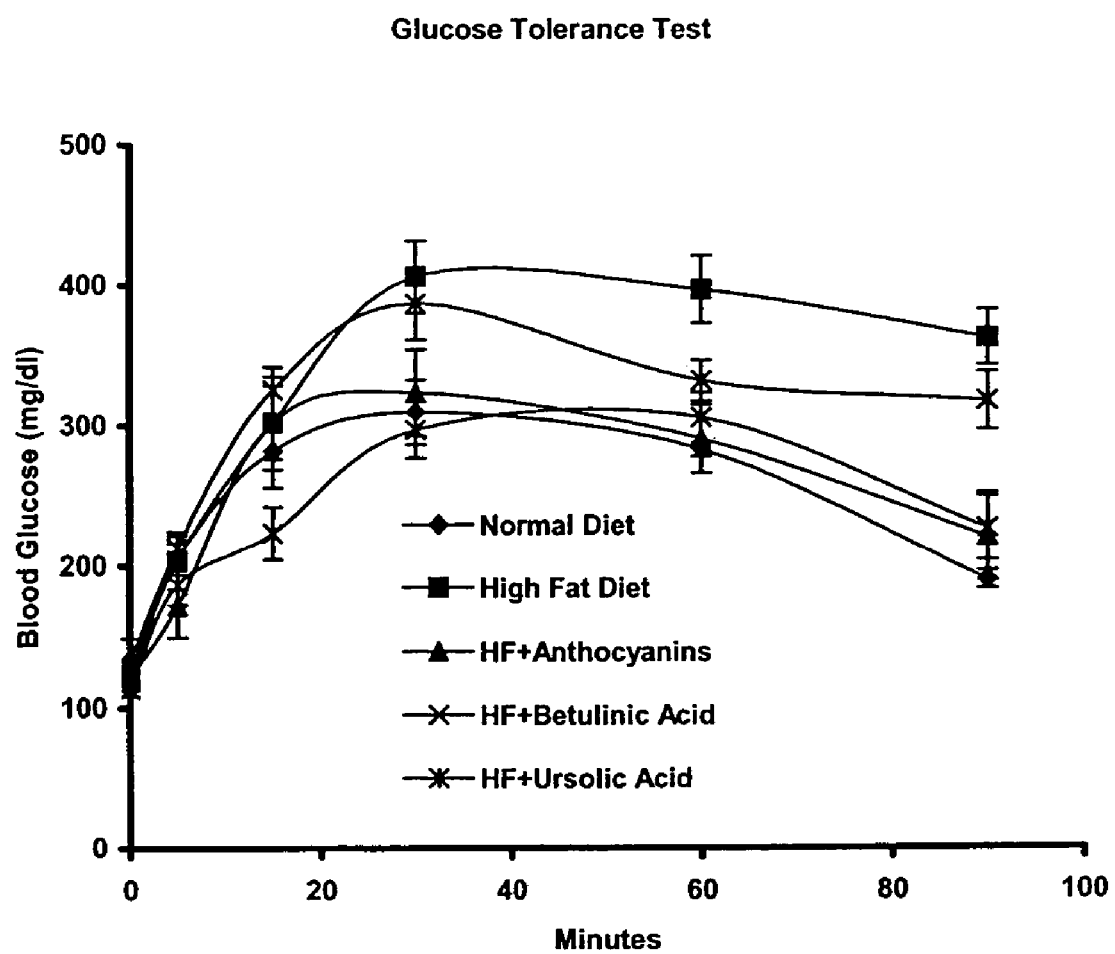
FIG. 6 is a graph showing results of Glucose Tolerance Test in obesity studies over a period of 90 min after the glucose load. The test was conducted during the $11^{th}$ the week of feeding. A solution of glucose (2 g/Kg body weight) in water was administered intraperitoneally and the blood glucose level was measured at 0, 5, 15, 30, 60, and 90 min. The blood was collected from tail vein. Vertical bars represents S.E. at each data point n=5.

Glucose tolerance test (GTT) was carried out on all animals to determine the insulin resistance (FIG. 6). Even though ursolic acid did not decrease bodyweight of the treated animals significantly, all animals in this group corrected glucose levels similar to control group animals fed on normal diet. The anthocyanin treatment showed similar effect as in the case of ursolic acid treatment in the GTT assay except that the blood glucose concentration reached the maximum at 30 min. The blood glucose level of the animals treated with ursolic acid (group 5) reached the maximum at 60 min indicating that ursolic acid may be delaying the glucose absorption. Therefore, ursolic acid may be a useful product to be consumed by type-2 diabetic patients since it has the ability to delay the absorption of glucose. At 90 min, the blood glucose levels of anthocyanin and ursolic acid treated animals were similar to the control group which received the low fat diet. However, the animals treated with betulinic acid did not respond in GTT and the results were similar to the control group fed on high fat diet. In the case of high fat diet fed animals, the blood glucose concentration reached the maximum at 30 min and stayed steady up to 90 min showing that these animals were insulin resistant.

Figure 4:
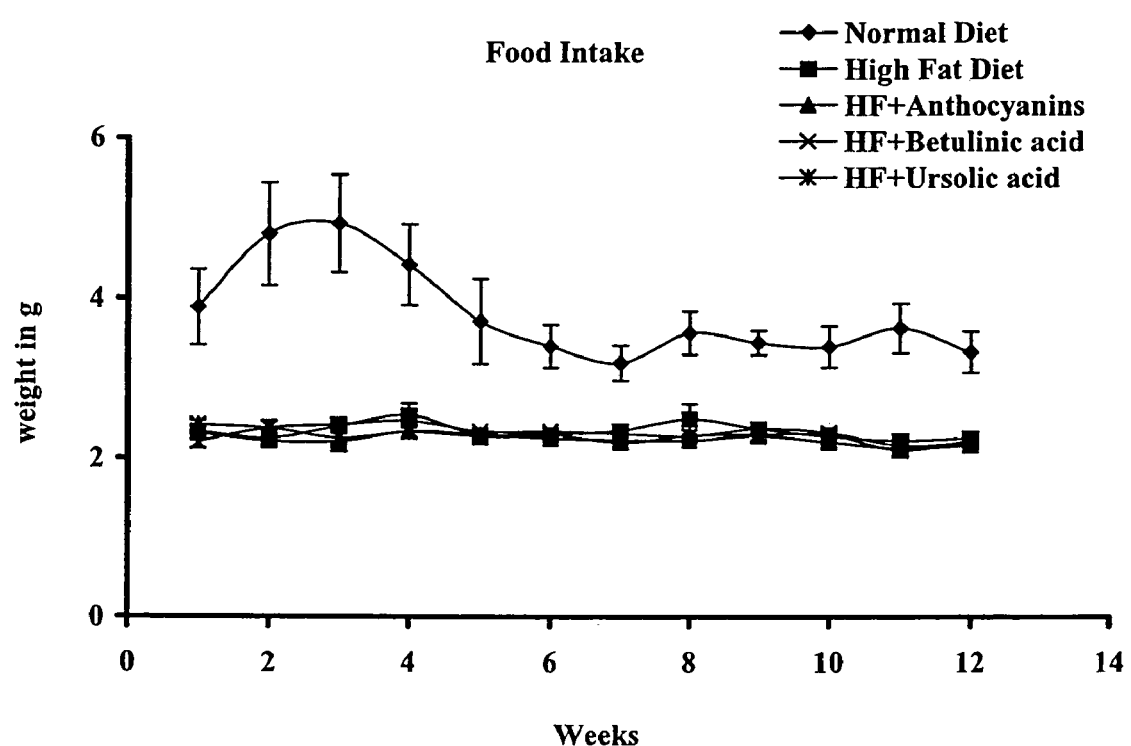
FIG. 4 is a graph showing the food intake (in g) of animals during the 12-week study period for obesity. Values are mean±SEM, n=8. Food intake was measured every day and averaged for every week. There was no significant difference among the high fat (HF, 60% K. Cal of fat) control and treatment groups. Treatment groups received high fat diet for 4 weeks before they were switched to diet mixed with test compounds, anthocyanins (1.0 g/Kg) betulinic and ursolic acids (0.5 g/Kg each) of high fat diet. The normal diet contained 10% K. Cal.
Figure 7:
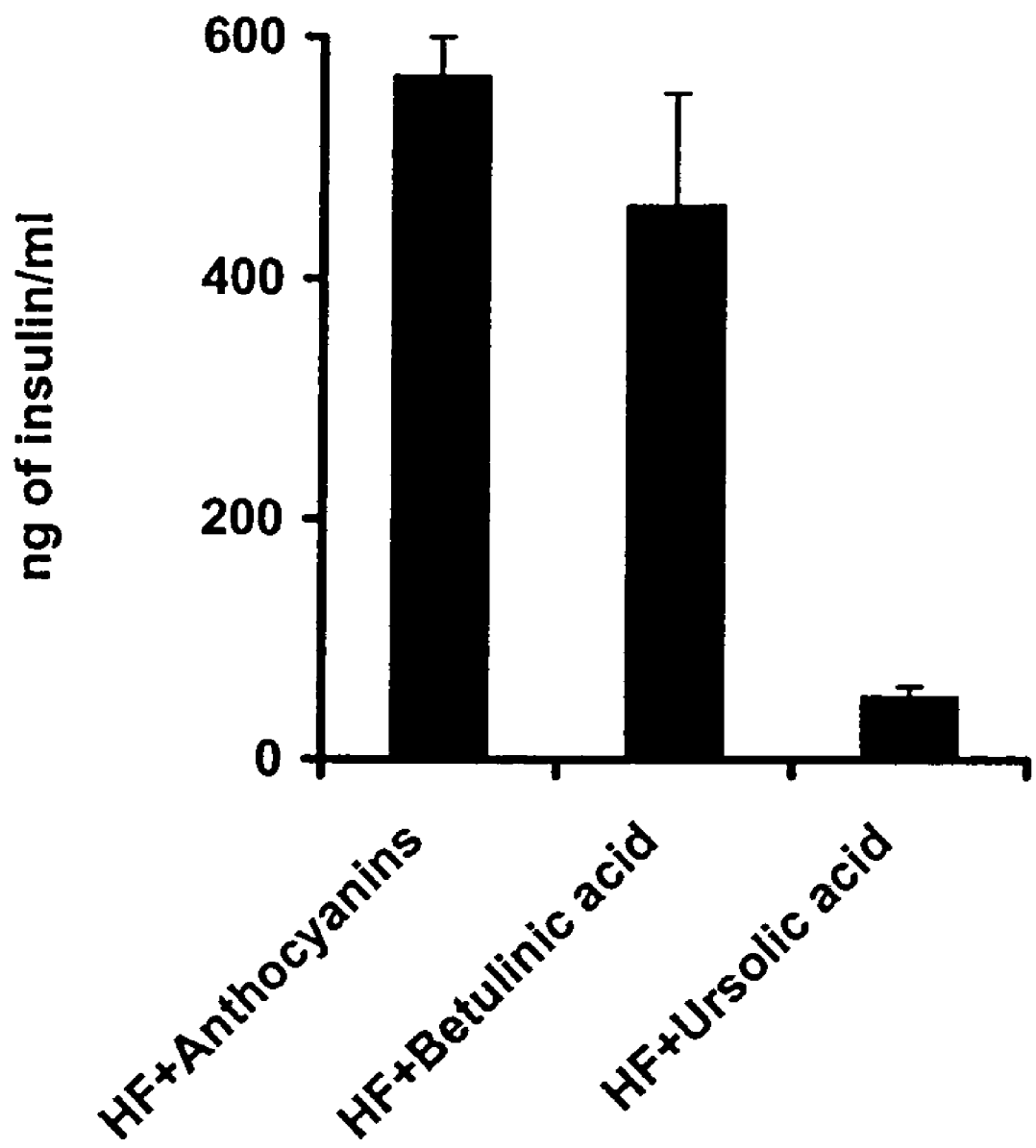
FIG. 7 is a graph showing plasma insulin levels of C57BL/6J mice determined at the end of the feeding experiment. The plasma insulin concentration determined for low and high fat fed control groups were 0.47±0.14 and 0.41±0.1 ng/mL, respectively. The quantification of insulin in plasma was carried out by Radio Immuno Assay (RIA). Each sample was assayed in duplicates and values represent mean±SEM for n=8.
Figure 8:
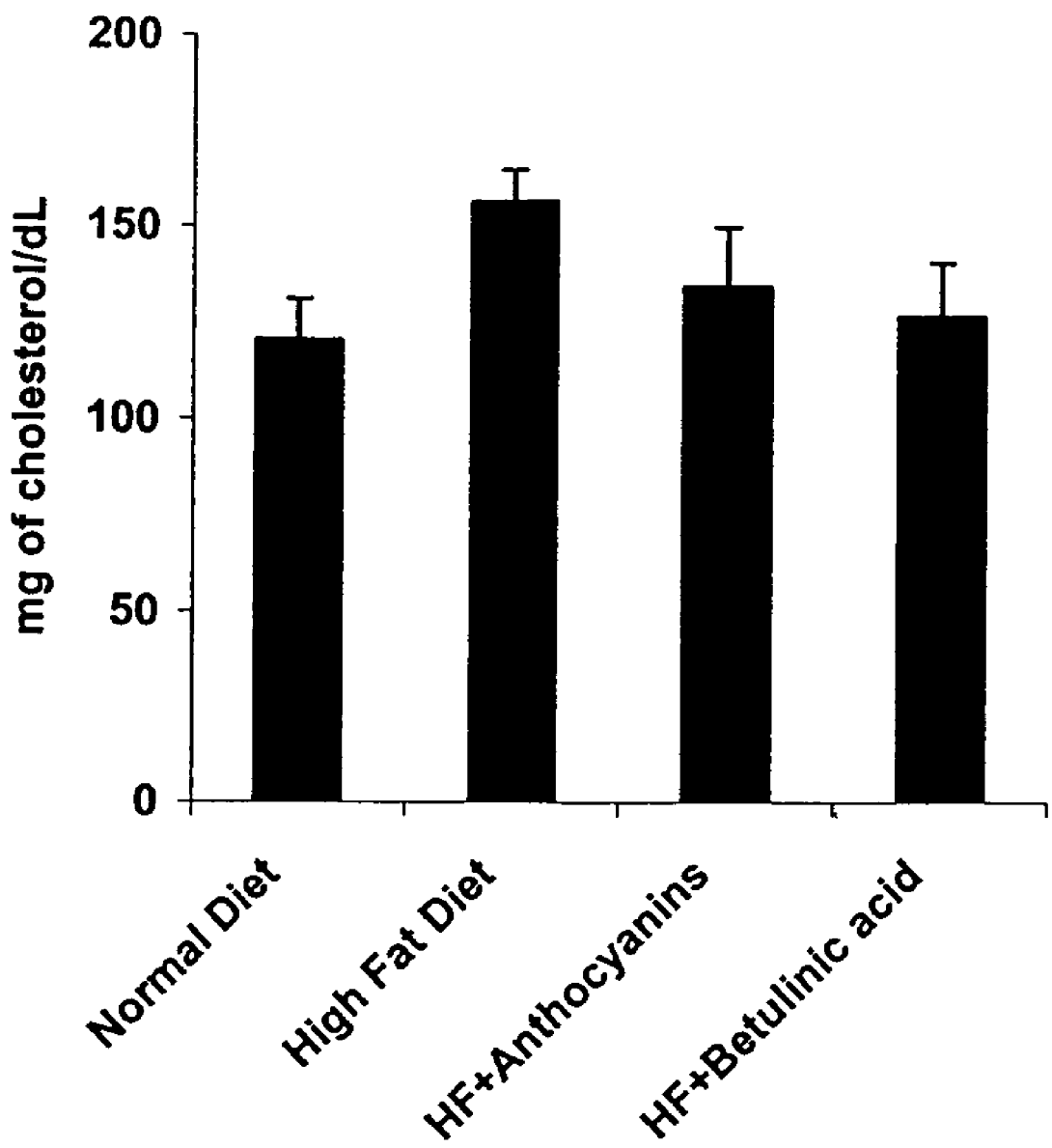
FIG. 8 is a graph showing plasma cholesterol level of mice in the plasma collected at the end of the feeding study and represented in mg/dL. The cholesterol level for ursolic acid treated animals was not tested due to insufficient amount of plasma sample. The values represent mean±SEM for n=4 or 5.
Figure 9:
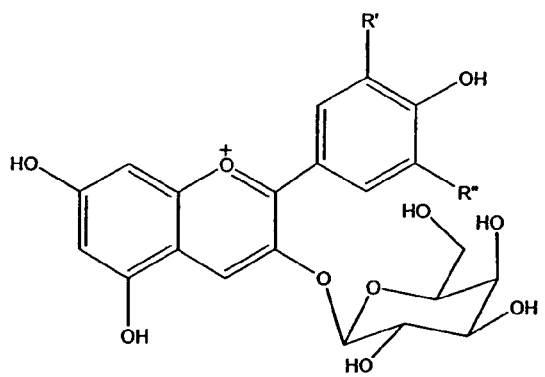
FIG. 9 shows the compounds isolated from 10 to 12 *Cornus mas* L.
Figure 9:
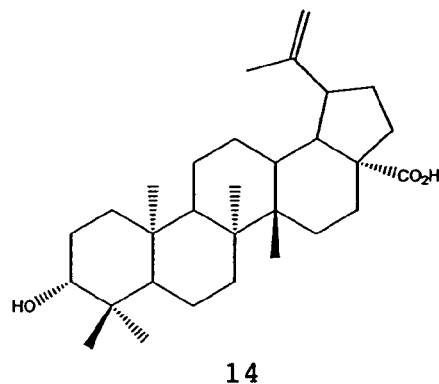
Figure 9:
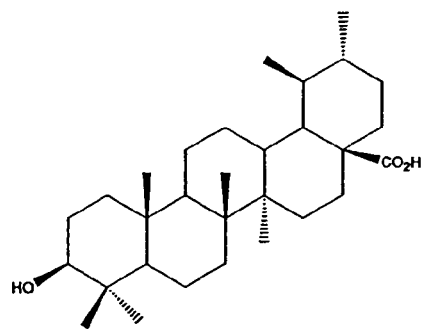

The plasma insulin concentrations of the animals treated with compounds 10-15 of FIG. 9 were considerably higher than the control animals received normal and high fat diets (FIG. 4). The increase in insulin secretion by anthocyanin treated animals was the highest among treatments. The insulin secretion by anthocyanin treated animals was 10 times or more than the ursolic acid treated animals (FIG. 7). In conclusion, the anthocyanins isolated from *C. mas* fruits was the best of three compounds studied in reducing the body weight of the animals on high fat diet. It also induced the secretion of an enormous amount of insulin without causing hypoglycemia.

The methods for the separation of and production of the anthocyanins and anthocyanidins are described in U.S. Pat. Nos. 6,194,469; 6,423,365; 6,623,743; 6,676,978 and 6,656,914; and U.S. patent application Ser. No. 10/084,575, filed Feb. 27, 2002 which are incorporated by reference herein in their entireties.

It is intended that the foregoing description be only illustrative of the present invention and that the present invention be limited only by the hereinafter appended claims.

We claim:

1. A method for treating obesity and insulin resistance in regulating of glucose in the blood in a mammalian patient in need of such treatment which comprises administering to said patient a composition of a purified mixture consisting of at least two molecules having structures

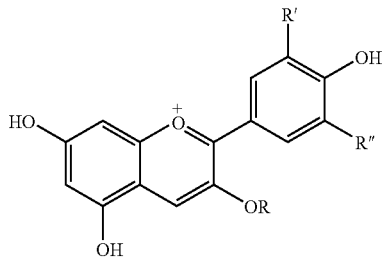

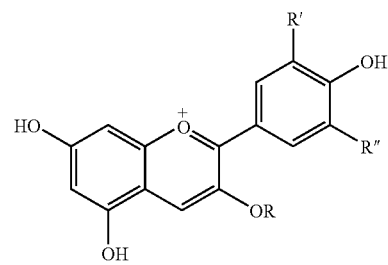

where R is H, glucosyl or galactosyl; R' is H, OH or OCH$_3$; and R" is H, OH or OCH$_3$ with the proviso that when R is H, then R' is not OCH$_3$ or R" is not OCH$_3$, or both R' and R" are not OCH$_3$ wherein one of the at least two molecules has R is galactosyl, R' is OH, and R' is H and is cyanidin-3-galactoside or one of the at least two molecules has R is galactosyl, R' is H, and R" is H and is pelargonidin-3-galactoside; and allowing the composition to treat the insulin resistance in regulating glucose and treat the obesity in the patient.

2. The method of claim 1 wherein said composition includes cyanidin-3-glycoside, delphinidin-3-galactoside, and pelargonidin-3-galactoside.

3. A method for the treatment of diabetes mellitus in an obese mammalian patient having insulin resistance in regulating blood glucose in need of such treatment which comprises administering to said obese mammalian patient a composition from a natural source of a purified mixture consisting of at least two molecules having structures

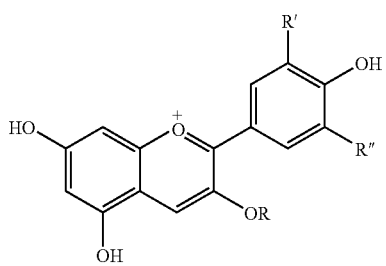

where R is H, glucosyl or galactosyl; R' is H, OH or OCH$_3$; and R" is H, OH or OCH$_3$ with the proviso that when R is H, then R' is not OCH$_3$ or R" is not OCH$_3$, or both R' and R" are not OCH$_3$ wherein one of the at least two molecules has R is galactosyl, R' is OH, and R' is H and is cyanidin-3-galactoside or one of the at least two molecules has R is galactosyl, R' is H, and R" is H and is pelargonidin-3-galactoside; and allowing the composition to regulate the blood glucose and treat the diabetes mellitus in the obese mammalian patient.

4. The method of claim 3 wherein the composition includes cyanidin-3-glycoside, delphinidin-3-galactoside, and pelargonidin-3-galactoside.

5. A method for treating obesity and insulin resistance to the regulation of glucose in the blood and treat hyperglycemia in a mammalian patient in need of such treatment which comprises administering to said patient a composition of a purified mixture consisting of at least two molecules having structures where R is H, glucosyl or galactosyl; R' is H, OH or OCH$_3$; and R" is H, OH or OCH$_3$ with the proviso that when R is H, then R' is not OCH$_3$ or R" is not OCH$_3$, or both R' and R" are not OCH$_3$ wherein one of the at least two molecules has R is galactosyl, R' is OH, and R' is H and is cyanidin-3-galactoside or one of the at least two molecules has R is galactosyl, R' is H, and R" is H and is pelargonidin-3-galactoside; and allowing the composition to treat the obesity, the insulin resistance and the hyperglycemia in the mammalian patient.

6. The method of claim 5 wherein said composition is isolated and purified from a fruit, a vegetable, or a flower.

7. The method of claim 5 wherein the composition includes cyanidin-3-glycoside, delphinidin-3-galactoside, and pelargonidin-3-galactoside.

8. The method of claim 5 wherein the composition is essentially free of sugars and acids present in the natural source.

9. A method for treating obesity and insulin resistance in regulating glucose in the blood and lipid disorders in a mammalian patient in need thereof which comprises administering to said patient a composition of a purified mixture consisting of at least two molecules having structures

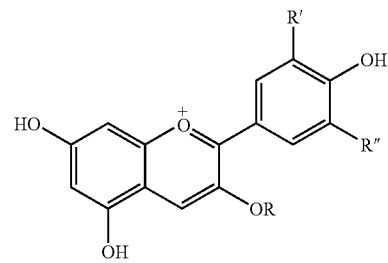

where R is H, glucosyl or galactosyl; R' is H, OH or OCH$_3$; and R" is H, OH or OCH$_3$ with the proviso that when R is H, then R' is not OCH$_3$ or R" is not OCH$_3$, or both R' and R" are not OCH$_3$ wherein one of the at least two molecules has R is galactosyl, R' is OH, and R' is H and is cyanidin-3-galactoside or one of the at least two molecules has R is galactosyl, R' is H, and R" is H and is pelargonidin-3- galactoside ; and allowing the composition to treat the obesity, insulin resistance and the lipid disorders in the mammalian patient.

10. A method for treating obesity and insulin resistance in regulating glucose in the blood and hypercholesterolemia in a mammalian patient in need of such treatment which comprises administering to said patient a composition of a purified mixture consisting of at least two molecules having structures

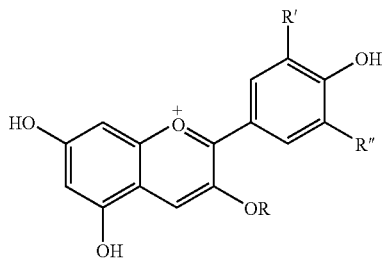

where R is H, glucosyl or galactosyl; R' is H, OH or $OCH_3$; and R" is H, OH or $OCH_3$ with the proviso that when R is H, then R' is not $OCH_3$ or R" is not $OCH_3$, or both R' and R" are not $OCH_3$ wherein one of the at least two molecules has R is galactosyl, R' is OH, and R' is H and is cyanidin-3-galactoside or one of the at least two molecules has R is galactosyl, R' is H, and R" is H and is pelargonidin-3-galactoside; and allowing the composition to treat the obesity, insulin resistance in regulating glucose and the hypercholesterolemia in the mammalian patient.

11. A method for treatment of obesity, insulin resistance in regulating of glucose in the blood and atherosclerosis in a mammalian patient in need of such treatment which comprises administering to said patient a composition of a purified mixture consisting of at least two molecules having structures

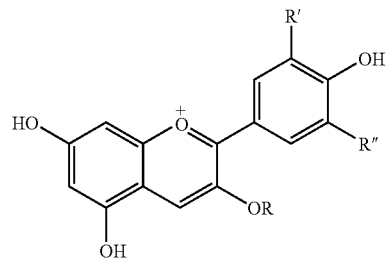

where R is H, glucosyl or galactosyl; R' is H, OH or $OCH_3$; and R" is H, OH or $OCH_3$ with the proviso that when R is H, then R' is not $OCH_3$ or R" is not $OCH_3$, or both R' and R" are not $OCH_3$ wherein one of the at least two molecules has R is galactosyl, R' is OH, and R' is H and is cyanidin-3-galactoside or one of the at least two molecules has R is galactosyl, R' is H, and R" is H and is pelargonidin-3-galactoside; and allowing the composition to treat the obesity, insulin resistance in regulating glucose and the atherosclerosis in the mammalian patient.

12. The method of claim 1 wherein said mammalian patient is a diabetic human and further comprising treating said diabetic human patient with a prescription drug for diabetes.

13. The method of claim 1 wherein the composition includes at least one molecule in which R is H.

14. The method of claim 1 further comprising administering ursolic acid.

15. The method of claim 1 further comprising administering betulinic acid.

16. The method of claim 1 wherein the composition is isolated from a natural source of *Cornus mas L.*

17. The method of claim 16 wherein the composition is essentially free of sugars and acids present in the natural source.

* * * * *